US010966672B2

(12) United States Patent
Nebosis et al.

(10) Patent No.: US 10,966,672 B2
(45) Date of Patent: Apr. 6, 2021

(54) SLIDING ARRANGEMENT FOR MOBILE TOMOSYNTHESIS X-RAY SYSTEM

(71) Applicant: AGFA NV, Mortsel (BE)

(72) Inventors: Rainer Nebosis, Munich (DE); Johannes Hoelzl, Munich (DE); Vladimir Zemanek, Munich (DE)

(73) Assignee: AGFA NV, Mortsel (BE)

( * ) Notice: Subject to any disclaimer, the term of this patent is extended or adjusted under 35 U.S.C. 154(b) by 0 days.

(21) Appl. No.: 16/491,242

(22) PCT Filed: Mar. 8, 2018

(86) PCT No.: PCT/EP2018/055735
§ 371 (c)(1),
(2) Date: Sep. 5, 2019

(87) PCT Pub. No.: WO2018/166880
PCT Pub. Date: Sep. 20, 2018

(65) Prior Publication Data
US 2020/0008763 A1 Jan. 9, 2020

(30) Foreign Application Priority Data
Mar. 17, 2017 (EP) .................................. 17161600

(51) Int. Cl.
*A61B 6/02* (2006.01)
*A61B 6/00* (2006.01)

(52) U.S. Cl.
CPC ............ *A61B 6/4405* (2013.01); *A61B 6/025* (2013.01); *A61B 6/4452* (2013.01); *A61B 6/4458* (2013.01); *A61B 6/4476* (2013.01)

(58) Field of Classification Search
None
See application file for complete search history.

(56) References Cited

U.S. PATENT DOCUMENTS

| 3,809,886 | A | | 5/1974 | Cochran et al. |
| 4,087,694 | A | * | 5/1978 | Hellstrom ................ A61B 6/02 378/181 |
| 4,139,776 | A | * | 2/1979 | Hellstrom ............ A61B 6/4476 378/181 |
| 9,795,347 | B2 | * | 10/2017 | Jan ....................... A61B 6/0487 |
| 10,039,508 | B2 | * | 8/2018 | Abramovich .......... A61B 6/025 |
| 2005/0226369 | A1 | | 10/2005 | Martin et al. |
| 2015/0117597 | A1 | * | 4/2015 | Jan ........................ A61B 6/025 378/20 |
| 2015/0265223 | A1 | | 9/2015 | Simon et al. |
| 2016/0287198 | A1 | * | 10/2016 | Abramovich .......... A61B 6/145 |
| 2020/0008763 | A1 | * | 1/2020 | Nebosis ................ A61B 6/025 |

OTHER PUBLICATIONS

Official Communication issued in International Patent Application No. PCT/EP2018/055735, dated Jul. 20, 2018.

\* cited by examiner

Primary Examiner — Thomas R Artman
(74) Attorney, Agent, or Firm — Stinson LLP

(57) ABSTRACT

A sliding arrangement for mobile X-ray devices enabling functionality for tomosynthesis acquisitions on systems without this functionality. The sliding arrangement substitutes a conventional X-ray collimator mount for fixing an X-ray collimator onto the gantry of a mobile X-ray system, and which adds the supplementary mechanical functionality that is required to perform tomosynthesis acquisitions.

11 Claims, 4 Drawing Sheets

SLIDING ARRANGEMENT FOR MOBILE TOMOSYNTHESIS X-RAY SYSTEM

CROSS REFERENCE TO RELATED APPLICATIONS

This application is a 371 National Stage Application of PCT/EP2018/055735, filed Mar. 8, 2018. This application claims the benefit of European Application No. 17161600.6, filed Mar. 17, 2017, which is incorporated by reference herein in its entirety.

BACKGROUND OF THE INVENTION

1. Field of the Invention

The invention generally relates to (retrofittable) subsystems for mobile X-ray devices enabling functionality for tomosynthesis acquisitions on systems without this functionality. Such a tomosynthesis subsystem is a part that substitutes a conventional X-ray collimator mount for fixing an X-ray collimator onto the gantry of a mobile X-ray system, and which adds the supplementary mechanical functionality that is required to perform tomosynthesis acquisitions.

2. Description of the Related Art

Tomosynthesis is a well-established method for performing high-resolution limited-angle tomography at radiographic dose levels. The technique is used for a variety of clinical applications, including vascular imaging, dental imaging, orthopedic imaging, mammographic imaging, musculoskeletal imaging, and chest imaging.

The concept of tomosynthesis is based on the application of reconstruction algorithms that are similar to CT reconstructions, but they differ in that they are based on performing an inverse Radon transform. Due to partial data sampling with very few projections, approximation algorithms have to be used. Filtered back projection and iterative, expectation-maximization algorithms have both been used to reconstruct the data. Reconstruction algorithms for tomosynthesis are different from those of conventional CT because the conventional filtered back projection algorithm requires a complete set of data. Iterative algorithms based upon expectation maximization are most commonly used, and thus relief the acquired dataset to span 180 degrees of a full circle. In practice, a tomosynthesis data set requires a limited number (e.g., 7-51) of discrete exposures, which are acquired under a limited rotation angle (e.g. between 15-60 degrees) around the volume of interest. In order to perform the reconstruction correctly and to achieve an acceptable reconstruction quality, it is important that the acquisition geometry of the different exposures are accurately known.

The incomplete set of projections is digitally processed to yield images similar to conventional tomography with a limited depth of field. After digital processing, a series of slices at different depths and with different thicknesses can be reconstructed from the image data set. However, since fewer projections are needed than CT to perform the reconstruction, radiation exposure and cost are both reduced. The acquisition of such a tomosynthesis data set is usually performed by exposing the patient and acquiring the data using a large-area digital detector, which is typically used for conventional radiography. A finite number of projection images are thus acquired over a limited angular range, which is accomplished by moving both the detector and X-ray source in opposing directions between the recording of the subsequent exposures, or by keeping the detector in a fixed position and only moving the X-ray source between the exposures. In applications where the detector is kept in a fixed position, it is known from the art that multiple spatially distributed X-ray sources may be used, or that movable X-ray sources are displaced into different positions.

While tomosynthesis is commonly applied as a functionality in fixed X-ray infrastructures, it is also a desirable application for mobile X-ray devices because of the advantages that tomosynthesis can offer (limited 3D-view at a cost of a patient dose which is much lower than a CT scan), especially in emergency environments. In order to be able to support tomosynthesis, the modality however needs to be able to support (preferably) automated movements that are typically not supported on a standard X-ray system. In other words, certain special adaptations are to be made.

Especially for mobile applications, the implementation of the tomosynthesis requirements represent a few particular technical challenges that however can be approached in different ways. US20150265223 for instance discloses a mobile tomography capable system wherein the X-ray source is displaced along a prescribed linear path in order to allow different subsequent acquisitions in a known acquisition geometry. In one embodiment, the entire mobile X-ray unit moves forwards by means of the wheels of the cart, so that the X-ray source moves in a stepped fashion to provide the linear and controlled displacement of the X-ray source along a prescribed path for collection of the subsequent acquisitions. In this embodiment, the X-ray source assembly remains fixed to the adjustable column through an intermediary boom apparatus. Another embodiment discloses a similar approach by enabling a similar motion by means of a controlled movement of one of the elements of the adjustable column or of the boom apparatus itself on which the X-ray source assembly is fixed. This movement can be performed by means of motorized extendable or rotatable structures of the supporting column or boom. In any case, the supported movements in these embodiments are limited by the rotational and translational capabilities of the mechanical elements supporting the X-ray source assembly, such as the adjustable column, the boom apparatus, and alike.

Another embodiment disclosed in the document implements a support track on which an X-ray source assembly can be moved along a linear path, and thus relieves the entire mobile X-ray unit itself to be moved between the acquisitions. Especially the latter embodiment solves the problem of stability during the movement. Moving the X-ray source along a support track is more stable and accurate in comparison with the movement of the entire X-ray cart on a floor surface that is not necessarily smooth. Moreover, the implementation of a motorized movement along such a support track allows a much more precise linear movement in comparison with movements of certain moving and articulating parts of the mobile X-ray device itself.

It is important to note that while the above embodiments are mechanically simple, in practice special precautions are to be taken in shielding off the patient tissue that is not subject of the examination. In other words, in order to prevent that unnecessary parts of the patient's body are being exposed to X-rays, radiation shielding has to be applied to the areas which risk to be exposed after the source movement to the next acquisition position. In case that the direction of the source assembly is not adjusted to the new relative position of the detector, the total exposure area will simply shift laterally and risks to expose unnecessarily additional patient tissue.

In the systems disclosed in the art, no physical modifications are made to the system for providing the tomosynthesis functionality. This may seem to be an advantage, but also has its limitations, namely that the tomographic movement is subject to the intrinsic mechanical limitations of the mobile X-ray systems. These limitations may be so severe or limiting in that they would not meet the requirements any longer for a proper image reconstruction. Examples of such limitations are for instance; inaccurate or rough movement capabilities of the mobile modality as a whole or of its moving parts contributing to the tomographic movement, inaccurate positional measurement capabilities that can link the positional geometry of the system sufficiently accurate.

SUMMARY OF THE INVENTION

The invention provides a sliding arrangement for mounting or retrofitting an X-ray source assembly on a supporting arm of a mobile X-ray unit, comprising a linear track comprising at least one linear rail supported by a rigid structure for mounting said arrangement onto said supporting arm, a carriage slidably mounted and movable along the length of said linear rail, said carriage comprising, a pivotable mounting interface for mounting said X-ray source assembly, characterized in that a tilting actuator adjusts the angle between the carriage and said pivotable mounting interface according to a position of the carriage along the linear rail, and wherein the angle between the carriage and said pivotable mounting interface is adjusted so that the center axis of an X-ray beam generated by said X-ray source assembly mounted on said carriage intersects with an isocenter at a distance d from the center of the sliding arrangement, in any of the positions of the carriage along the sliding track.

The invention thus concerns a sub-part or element intended for integration into new mobile X-ray system configurations or integration onto existing mobile X-ray systems, hereby providing the tomosynthesis functionality as a retrofitted solution. The sub-part offers an easy way to provide the required mechanical functionality to enable tomosynthesis image acquisition.

The conventional approach to solve the problem of supporting a limited arc angular acquisition sequence for tomosynthesis on a mobile X-ray modality is to use the rotation capability of a rotating c-arm structure. While this seems at first sight to be a plausible and technically feasible solution, certain mechanical limitations of the C-arm structure do not allow such implementation in practice. The weight of the X-ray source assembly, for instance, does not allow the C-arm arc to be rotated beyond certain angles around its inclination point. The tilt angle of the C-arm structure around this inclination point may in practice be mechanically limited to prevent damage to the system or to prevent a potential conflict with the patient. A main disadvantage of a C-arm is that this configuration cannot work in combination with standard hospital beds as the detector must be positioned under the bed; there is typically not enough room to accommodate the detector in combination with the part of the C-arm to which it is attached. Moreover, the hospital bed is typically not transparent for x-rays. This particular problem is the main argument why rotating arc is not the preferred solution to acquire tomosynthesis sequences on a mobile system. A solution to this would be a half C-arm wherein not the detector, but only the X-ray source assembly is mounted to the C-arm. In this case the panel would be positioned directly underneath the patient which is lying in bed. But, especially in this kind of configuration, the C-arm would no longer be balanced and would cause other mechanical and safety challenges to the configuration. Tomosynthesis reconstruction requires accurate knowledge of the acquisition geometry for good results, or requires a reconstruction algorithm that is sufficiently robust against positioning errors.

As such, a different approach is taken compared to the solutions described in the art by adding this supplementary component to the system solving above mentioned problems. It is acknowledged that the stability of the resulting construction may be challenged when adding a weighty element to an existing structure, and also that the support track itself needs to be foreseen with the necessary features to ensure that the center of the X-ray beam is aligned to the surface of the detector panel when the X-ray source assembly is moved along the track. However, as will be demonstrated, the integration of the sliding arrangement of the invention resolves the problems around the required accuracy and mechanical functionality.

An important aspect to be resolved in a tomosynthesis implementation with a sliding arrangement remains the fulfillment of the requirement for the X-ray beam from the X-ray source assembly to be oriented towards the center of the detector surface. Since, in a mobile setting, the detector is usually positioned underneath or behind the patient—and thus is not moved between the different acquisitions-, the center of the X-ray beam needs to be targeted towards the center of the detector surface for all acquisition steps.

In the context of this invention, the term sliding arrangement refers to an arrangement or configuration that is intended to provide sliding functionality to an X-ray source assembly when integrated in an X-ray system; the arrangement or system enables an X-ray source assembly of an X-ray system to slide along a linear track. The set of parallel and linear rails is also referred to as a linear track. The X-ray source assembly is a combination of an X-ray source and collimator. An X-ray source assembly is in many technical implementations a tightly integrated entity of an X-ray source and a collimator (or beam limiting device). The X-ray source is in the most conventional meaning an X-ray tube, but could in principle be any other type of X-ray source. As such, the sliding arrangement essentially refers to the combination of a set of linear rails and a carriage mounted to these rails to which the X-ray source assembly is attached.

The carriage is in this arrangement connected to a linear actuator that causes the movement of the carriage along the track. The linear actuator pushes or pulls the carriage in any of the two directions of the linear track. The linear actuator is a mechanical component that acts on the carriage and causes the linear movement. The linear actuator may be electrically powered or may be driven manually.

The carriage comprises a pivotal connective element or interface for the X-ray source assembly, referred to in this application as pivotable mounting interface. X-ray source assemblies have in practice well defined mechanical interface connectors for mounting them onto a stand or boom of an adjustable column, or to the above mentioned pivotal connective element. The interface comprises a mechanism to adjust the emission point of the x-ray source to the rotational axis of the pivotable mounting plate.

Next to the requirement for tomosynthesis acquisitions that the X-ray source should be able to perform a defined and known trajectory, it is desirable that the X-ray source either revolves around the detector surface center at a fixed distance (which could be achieved by alternative tomosynthesis setups) in order to span a number of degrees of rotation around said detector surface, or that the X-ray source performs a linear trajectory while maintaining a fixed focus point.

Further advantages and embodiments of the present invention will become apparent from the following description and drawings.

DETAILED DESCRIPTION OF THE PREFERRED EMBODIMENTS

Figure 1:
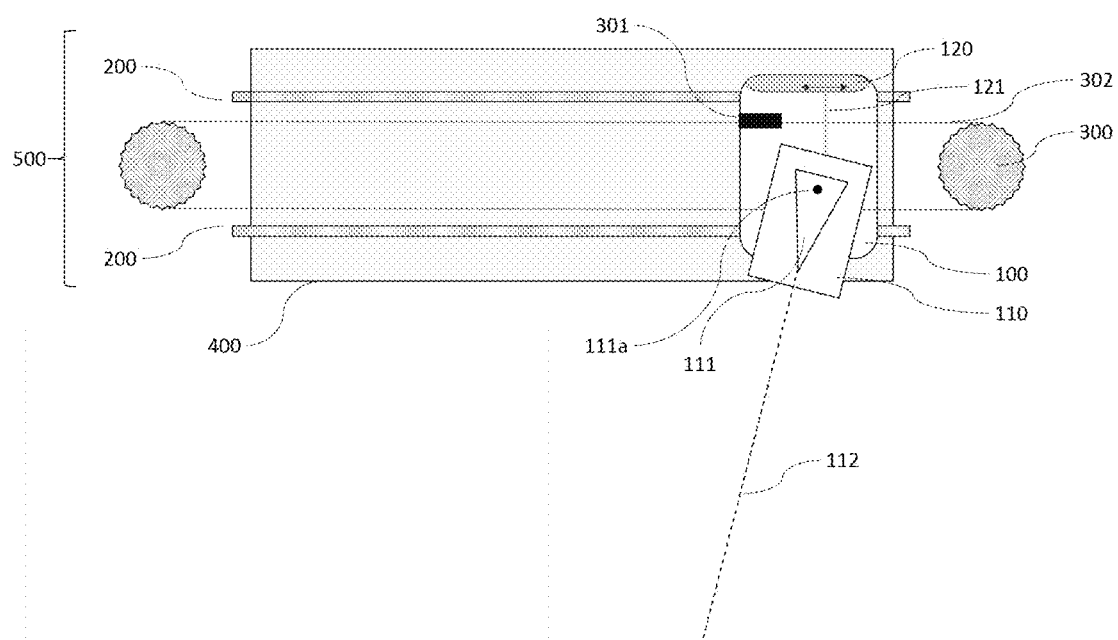
FIG. 1 shows a schematic overview of an embodiment of the sliding arrangement [500] of the invention. In this embodiment, two parallel linear rails [200] are mounted on a rigid structure [400] and make up a linear track for the carriage [100]. The rigid supporting structure [400] serves as an interface with the supporting arm of the mobile X-ray device. The carriage [100] is fitted with a pivotable mounting interface [110] that can accommodate the weight of an X-ray source assembly [111]. The pivoting movement of the mounting interface [110] is controlled or actuated by a connecting rod or tilting actuator [121] which can be driven by a servo motor [120]. The angle of the pivotable mounting interface [110] directly impacts the direction of the center of the X-ray beam [112] generated by the X-ray source in the assembly [111]. A mechanism is provided to adjust the X-ray emission point [111a] to the rotation axis of the carriage [100]. The movement of the carriage [100] along the length of the linear track is effected by a linear actuator [302] comprising a belt which is attached to a nut (or fixation) [301] to apply the driving force to the carriage. The belt or chain is in its turn driven by a set of wheels [300].

The sliding arrangement of the invention is intended to be mounted onto a conventional supporting arm for an X-ray source assembly of an X-ray device. In most cases, the sliding arrangement is made of mainly metal parts to provide the necessary rigidity to the component. Especially the rigid structure [400] is preferably composed of metal parts and can be conceived as a simple bare metal pane that can be fitted to the supporting arm, and which accommodates the preferably metal linear rails [200]. To reduce weight, other rigid but more lightweight materials like fiber reinforced composites or plastics can be used for the rigid support structure [400] and guiding rails (e.g. friction bearings) [200].

The sole additional requirement towards the X-ray device for allowing the sliding arrangement to be mounted is sufficient strength of the supporting arm for carrying the additional weight of the sliding arrangement. This weight can however be significantly reduced using fiber reinforced materials. The device can be mounted to static room-integrated X-ray devices, but it is specifically suitable to substitute the default mounting interface of the X-ray source assembly of a mobile X-ray system. As such, the sliding arrangement will be fixed between the supporting arm and the X-ray source assembly, and will thus serve as a mounting interface for the X-ray source assembly. In this type of configuration, the sliding arrangement is firmly mounted to the end of the supporting arm such that it is safely fitted to provide sufficient stability to the combination of the sliding arrangement and the X-ray source assembly. The type of fixation interface to fix the sliding arrangement to the supporting arm ideally allows some flexibility in the final positioning or orienting the sliding arrangement to a certain extent. For instance, a ball head joint could be used to make this connection and still allow this flexibility.

The sliding arrangement of the invention comprises a number of essential components, being the carriage accommodating the pivotable mounting interface, a linear track (which may comprise one or more parallel linear rails), a linear actuator actuating the movement of the carriage along the linear track, and a mechanism or provision that controls the tilting movement of the mounting interface so that the X-ray beam center points to the same isocenter position p at different possible positions of the carriage on the linear track.

The linear (sliding) track is typically implemented as a set of parallel (and preferably) metal bars which are mounted in a parallel configuration so that they provide stable support for the wheels or friction reducing elements of a carriage to which the X-ray source assembly is mounted. Alternatively the linear sliding track can comprise rigid rods (e.g. fiber reinforced plastic rods) and friction bearings.

The type, shape and number of rails will determine to a great extend the type of connection or contact that the carriage will have with the rails to provide the sliding functionality of the carriage along the linear track. Different types of configurations can be envisaged using a combination of wheels rolling on the tracks, a combination of a set of clamps (at least 1) made of a friction reducing material (such as Teflon) which clamp around and slide along the shape of the rails, or a set of sliding nuts (at least 1) similarly made of a friction reducing material (such as Teflon) sliding around a metal rod or bar. In any case the rails determine how the carriage will make contact with the rails, and how it can provide the required stability during the linear (sliding) movement.

Figure 4:
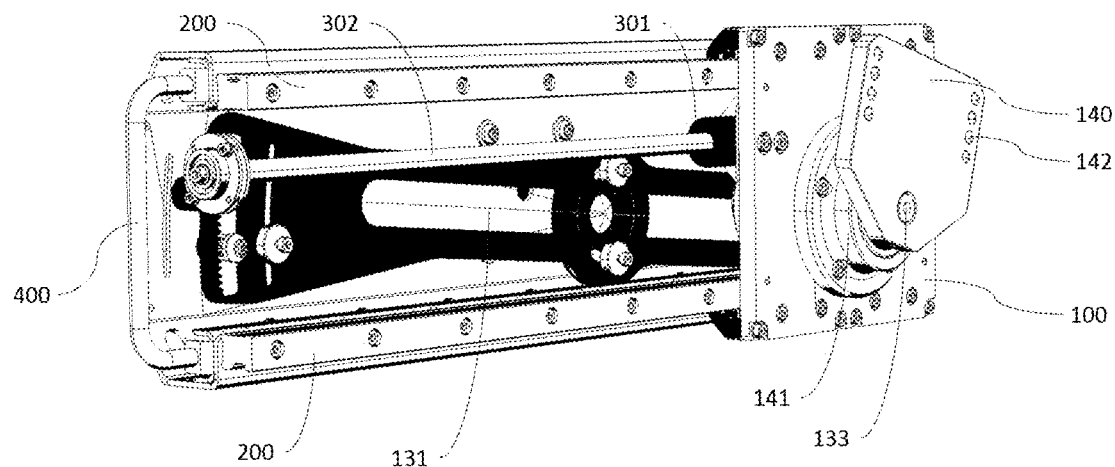
FIG. 4 shows a perspective view of the front side of a preferred embodiment of the invention and shows the sliding arrangement [500] with its main components: the carriage [100] fitting the pivotable mounting interface [140] by means of the rotation axis [133] and caught in a ball bearing set [141], adjustment means [142] to align the x-ray emission point [111a] and the rotation axis [133], two parallel rails [200] making up the linear track, the ball screw of the linear actuator [302], the spindle nut [301] attached to the carriage and a linear guiding slit (or motion link) [131] (shown in a tilted position). [400] indicates an element of the rigid structure.
Figure 5:
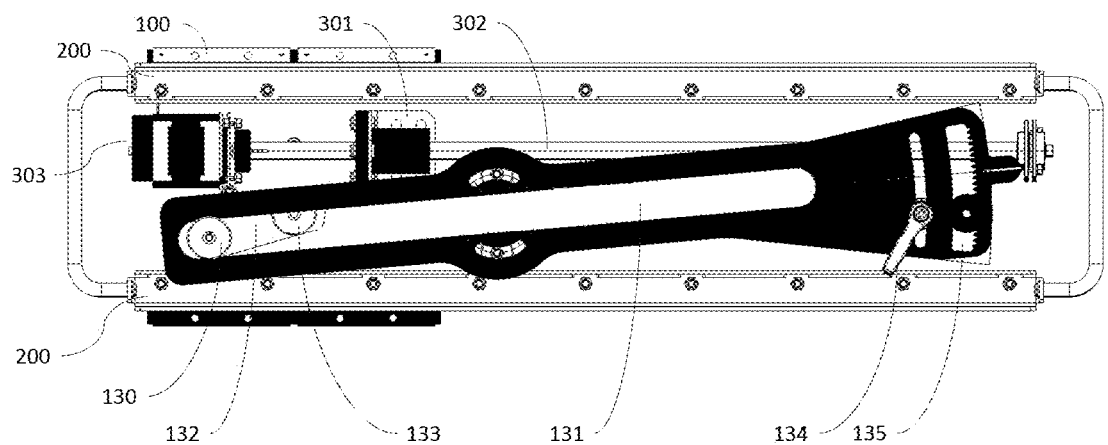
FIG. 5 shows a perspective view of the back side of the same preferred embodiment as in FIG. 4, showing the same components, but additionally giving a better view on the guiding slit [131] which fits a circular shaped pin [130] attached to the crank [132] which is attached to the center of the rotation axis [133] of the pivotable mounting interface [140]. [135] shows an angle adjusting gearing to adjust the angle of the guiding slit (or motion link) [131] relative to the direction of the linear track. The lever [134] allows to lock the rotation of the guiding slit into a fixed position.
Figure 6:
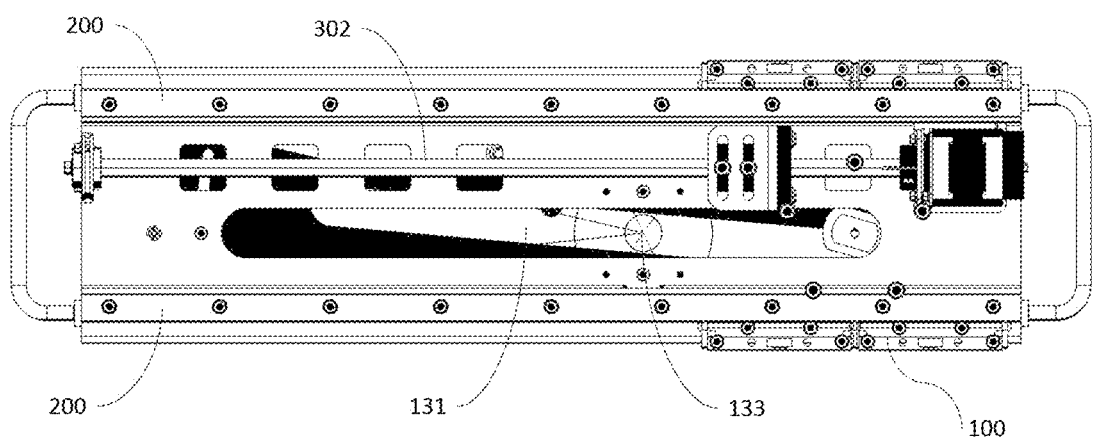
FIG. 6 shows another perspective view of the front side of a preferred embodiment of the invention.

In a preferred embodiment, the carriage comprises a set of 4 wheel set arrangements which are mounted per pair at opposite sides of the carriage (see FIG. 4-6). The wheels themselves are not visible in the figure, but are hidden at the inside of the wheel set arrangements. The wheels are making contact with the metal rail [200] in a U-shaped groove at the outer edges of the rail. The shape of the rails prevent that the carriage falls off the linear track, as it is clamped around it in its entirety. In other words, the wheels are clamped around the outer surfaces of the 2 rails so that they make contact with the rails in an opposing way. As such, the track-and-carriage configuration can provide the necessary mechanical support to carry the weight of the X-ray source assembly. Alternatively, the wheels can be arranged such that they rest on the upper surface of the rails, so that they are pushed downwards against the upper surface of the rails by gravity. The first embodiment described in this paragraph is however preferred, as the carriage cannot fall off the rails and is attached to them under all possible orientations of the rails.

In another embodiment, the rails can be conceived as a set of parallel cylindrical or rectangular bars to which the carriage is attached by means of a set of rings or nuts adapted to the shape of the cross-sections of the bars and that can slide along the length of the bars. The material of the rings or nuts sliding along the length of the bars again has to be made of a material that reduces the friction between the sliding part and the metal bars. In such a configuration, it can be envisaged that only 1 bar could be used as well when properly shaped and adapted to the carriage.

The carriage can be moved along the length of the linear track so that the X-ray source assembly can assume different positions (and expose the object or patient under different incidence angles) with respect to the center of the detector. In practice, a sufficient length for the linear track can be as low as 20 cm, this is considered to be sufficient to suite the requirements for a mobile tomosynthesis application offering a minimal depth resolution after reconstruction. Nevertheless, a higher length (between 20 to 50 cm) would yield better results with respect to the resolution at different depths after reconstruction. In this respect, a tradeoff has to be made between the image quality and the consequences of the additional weight (and volume) of sliding arrangement. The SID (source image-detector distance) in the example above is in the range of 100-130 cm, which corresponds to similar distances of the measure d used in the drawings. While the distance d corresponds to the distance between the linear track and the detector surface, the SID corresponds to the distance between the detector surface and the source (which is a virtual point somewhere within the X-ray source assembly—the X-ray emission point [111a]).

In order to accurately determine and change the incidence angle of the X-ray beam according to the different positions of the carriage along the sliding track in order to focus the X-ray beam centers in one point, the carriage is foreseen with a mechanism that allows the mounted X-ray source assembly to pivot around an axle [133] to align the X-ray beam center to the center of the detector under all circumstances (i.e. along the different possible positions along the track).

In one embodiment of the invention, the element that enables the rotation of the pivotable mounting interface in relation to the carriage consists of a pivoting axle [133] that fits through the body of the carriage, so that both ends of this pivoting axle come out on either sides of the carriage body. The pivoting axle [133] is preferably caught in a ball bearing set [144] to ensure stable movement considering the weight of the X-ray source assembly. The pivoting axle [133] itself provides the connection between pivotable mounting interface that is fixed to it on one side of the carriage, and to the crank [132] that is located at the opposite side of the carriage. The pivotable mounting interface is fixed to the pivoting axle and further comprises a mounting plate adapted to receive and fixate the X-ray source assembly firmly. As such, the pivotable mounting interface is rotatably fixed to the crank [132], so that both elements cannot rotate with respect to each other.

As explained above, located on the other side of the carriage, the crank [132] is fixed to the same pivoting axle as the mounting interface [110] and, in one embodiment, comprises a circular shaped pin [130] at the end furthest away from the pivoting axle. This circular shaped pin is dimensioned so that it fits into a guiding slit [131], and can slide along the length of this guiding slit. As such, the guiding slit guides the circular pin during the movement of the carriage along the linear rail [200] and levers the crank into a certain angle with respect to the linear track. The shape of the guiding slit [131] thus determines the relative angle of the crank (and connected to it, the pivotable interface) with respect to the linear track [200] during the translation of the carriage along the linear track. The mechanism of the pin gliding in the guiding slit thus determines the rotation angle of the pivotable mounting interface and the X-ray source assembly.

Considering a typical length of the linear track of about 20 cm and an SID of 100-130 cm for a standard mobile X-ray device, a purely linear shape of the guiding slit [131] enables that the X-ray beam central axes intersect in a single point with sufficient accuracy for the (tomosynthesis) application. This remains valid for all configurations where the length of the linear track maintains the same proportion to the SID. In case that the SID becomes smaller relative to the length of the linear track, the shape of the guiding slit [131] may need to be adapted to a slightly sigmoid shape in order to ensure that the X-ray beam centers intersect in a single point.

So, a short sliding arrangement with a short linear track is advantageous in that the shape of the guiding slit can be purely linear, but it also has the advantage that the total weight of the assembly is kept minimal.

Figure 2:
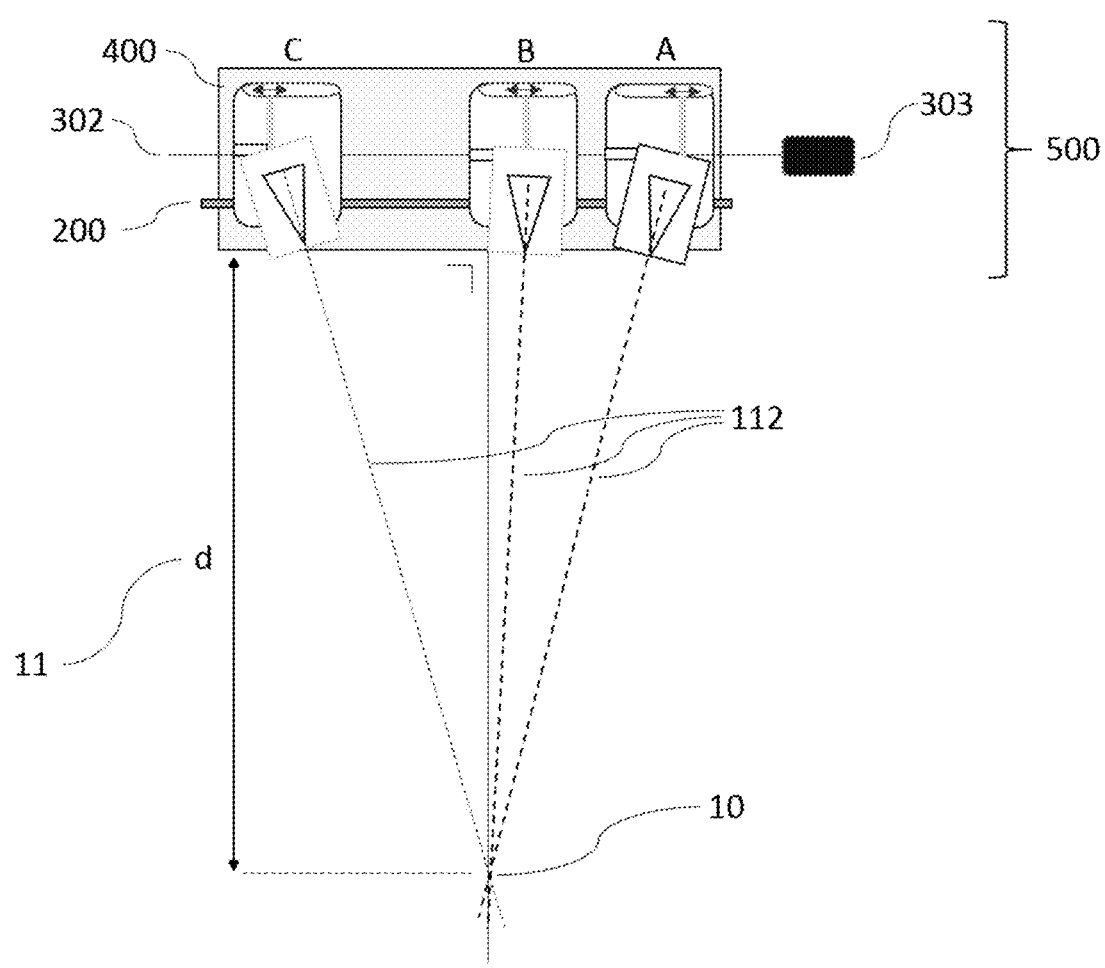
FIG. 2 shows another sliding arrangement [500] differing from the embodiment in FIG. 1 in that the sliding track is composed of a single linear rail [200] mounted to the rigid structure [400]. In this figure, 3 different positions of the carriage [100] are depicted as "A", "B" and "C". In each of these positions, the angle of the mounting interface is adapted such that centers of the X-ray beams generated at these positions [112] coincide in an isocenter or incidence point [10] at a distance d [11]. The linear actuator [302] to drive the movement of the carriage [100] comprises an electric motor [303] driving a ball screw or spindle and according ball or spindle nut [301] which is attached to the carriage.
Figure 3:
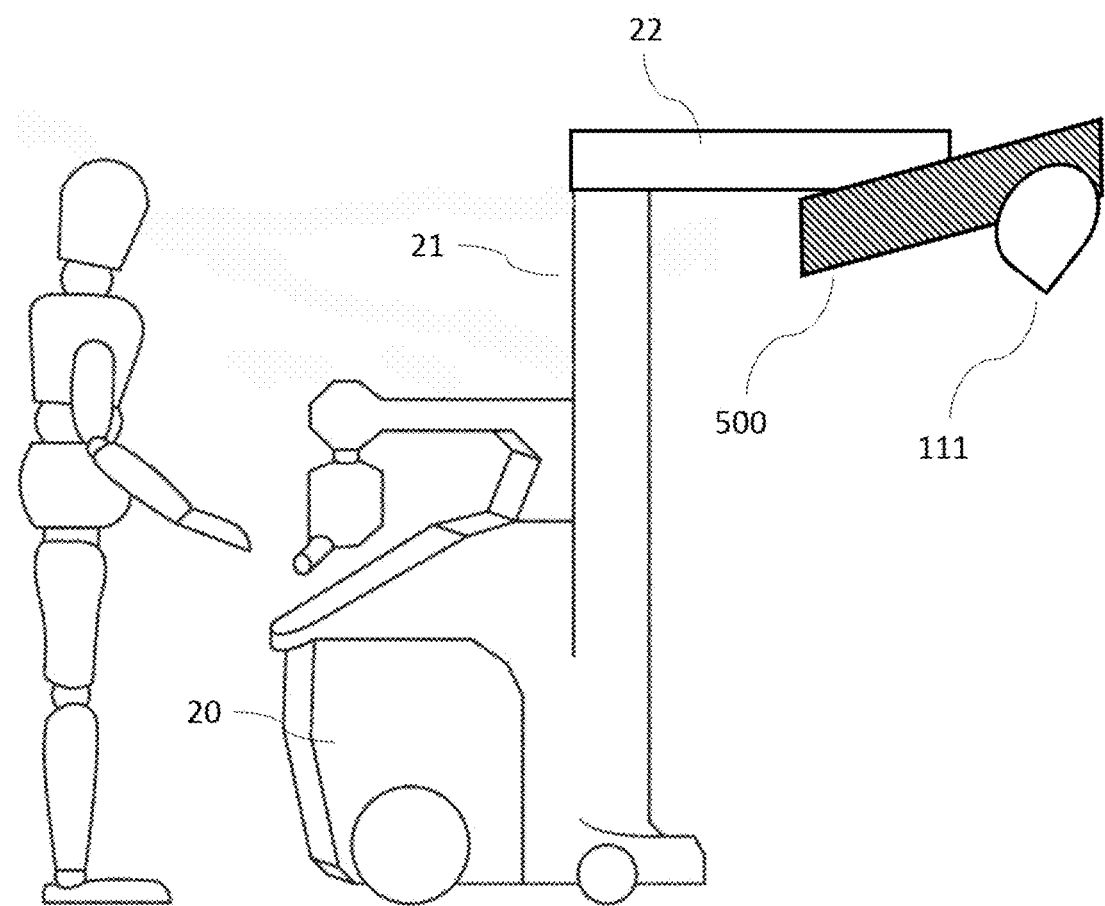
FIG. 3 depicts the sliding arrangement [500] of the invention in conjunction with the other components of a mobile X-ray device [20]. Where [500] represents the sliding arrangement of the invention mounted to a supporting arm [22] which is in itself mounted on a stand [21]. [111] represents the X-ray source assembly mounted onto the sliding arrangement [500].

Besides the shape, also the selection of the orientation of the guiding slit [131] allows to influence the rotational behavior of the pivotable mounting interface along the linear track. One option to adapt the angulation speed (the amount of rotation of the pivotable mounting interface expressed in degrees per traveled cm of the carriage along the linear track) of the mounting interface with respect to the linear track is to increase or decrease the "slit-tilt", which is the angle between the guiding slit [131] and the linear track. In case that the guiding slit is oriented in parallel with the linear track, the pivotable mounting interface will not rotate at all when the carriage progresses. Increasing the "slit-tilt" will however increases the pace at which the angle varies with changing the position of the carriage on the linear track. When the guiding slit is linear, increasing the angle slightly will result in shortening the distance d. The more the "slit-tilt" angle is increased, the shorter the distance d will get. In other words: the orientation (angle) of the guiding slit determines the amount of tilt at the different positions of the X-ray source assembly (FIG. 2: A, B & C). Changing this tilt angle allows adjustment to different SID values to ensure a common intersection point [10]. For increasing SID values the tilt of the guiding slit must decrease.

An angle adjusting gearing [135] can be optionally foreseen to adjust or drive the "slit-tilt" angle by means of a gearing set. An angle adjustment lock [134] can be foreseen to maintain the position of the slit [131] in a more reliable way.

Besides the mechanical embodiment described above where a mechanical interface allows the mounted X-ray source assembly to pivot around an axle [133] to align the X-ray beam center to the center of the detector under all circumstances (i.e. along the different possible positions along the track), alternative embodiments for tilting the pivotable mounting interface may be envisaged. One example of such an alternative (refer to FIG. 1) is that the pivoting of the pivotable mounting interface is driven by an electrically powered servo motor [120] selectively driven to adopt different angles depending on the position of the carriage on the linear track. In this case, the measurement of the position of the carriage on the linear track is effected by means of for instance a linear encoder, a digital caliper, an infra-red based range sensor, or other methods known in the art. The pivoting movement of the mounting interface [110] is controlled or actuated by a connecting rod or tilting actuator [121] which is then driven by the servo motor [120] which in its turn is controlled by a controller interpreting measured positional data of the carriage on the linear track. Controllers performing this function are known in the art and may be conceived as analog or digital circuits.

In addition the different actuators can comprise a module to determine the position or orientation of an actuator (position encoder) or the actuator itself can be designed to output position or orientation information directly (e.g. stepper motor). This information can be used as input for the reconstruction and/or to set an electrical or digital ratio between the linear and rotational movement—in case the rotational motion is realized with a separate actuator.

The invention claimed is:

1. A sliding arrangement for mounting an X-ray source assembly on a supporting arm of an X-ray unit, the sliding arrangement comprising:
    a linear track including a linear rail supported by a structure that mounts the sliding arrangement onto the supporting arm;
    a carriage slidably mounted and movable along a length of the linear rail, the carriage including a pivotable mounting interface that mounts the X-ray source assembly;
    a tilting actuator that adjusts an angle between the carriage and the pivotable mounting interface based on a position of the carriage along the linear rail,
    and that includes a pin configured to be guided by a guiding slit to actuate a crank fixed to a rotation axis of the pivotable mounting interface during linear movement of the carriage along the linear rail; and an angle adjusting gearing that adjusts an angle between the guiding slit and the linear rail; wherein
    the angle between the carriage and the pivotable mounting interface is adjustable so that a center axis of an X-ray beam generated by the X-ray source assembly mounted on the carriage intersects with an isocenter at a distance d from a center of the sliding arrangement at any position of the carriage along the linear rail.

2. The sliding arrangement of claim 1, further comprising a linear actuator connected to the carriage.

3. The sliding arrangement of claim 2, further comprising a controller configured or programmed to drive the tilting actuator based on the position of the carriage along the linear rail.

4. The sliding arrangement of claim 2, further comprising a motor that drives the linear actuator.

5. The sliding arrangement of claim 2, further comprising a fixing lever that fixes an angle between the guiding slit and the linear rail.

6. The sliding arrangement of claim 2, wherein the guiding slit has a linear, non-linear, or sigmoid shape.

7. The sliding arrangement of claim 2, wherein the angle between the guiding slit and the linear rail is based on the distance d.

8. The sliding arrangement of claim 1, further comprising a controller configured or programmed to drive the tilting actuator based on the position of the carriage along the linear rail.

9. The sliding arrangement of claim 1, further comprising a fixing lever that fixes an angle between the guiding slit and the linear rail.

10. The sliding arrangement of claim 1, wherein the guiding slit has a linear, non-linear, or sigmoid shape.

11. The sliding arrangement of claim 1, wherein the angle between the guiding slit and the linear rail is based on the distance d.

* * * * *